United States Patent
Basinger

(10) Patent No.: US 9,420,384 B2
(45) Date of Patent: Aug. 16, 2016

(54) AUTOMATIC GAIN CONTROL FOR IMPLANTED MICROPHONE

(71) Applicant: David L. Basinger, Loveland, CO (US)

(72) Inventor: David L. Basinger, Loveland, CO (US)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 14/171,647

(22) Filed: Feb. 3, 2014

(65) Prior Publication Data

US 2014/0221729 A1    Aug. 7, 2014

Related U.S. Application Data

(63) Continuation of application No. 12/357,183, filed on Jan. 21, 2009, now Pat. No. 8,641,595.

(60) Provisional application No. 61/022,390, filed on Jan. 21, 2008.

(51) Int. Cl.
*H04R 25/00* (2006.01)
*A61N 1/36* (2006.01)

(52) U.S. Cl.
CPC .......... *H04R 25/505* (2013.01); *A61N 1/36032* (2013.01); *H04R 25/606* (2013.01)

(58) Field of Classification Search
CPC ... A61N 1/36032; H03G 3/342; H04R 25/00; H04R 25/356; H04R 25/453; H04R 25/50; H04R 25/505; H04R 25/558
See application file for complete search history.

(56) References Cited

U.S. PATENT DOCUMENTS

| | | |
|---|---|---|
| 4,630,302 A | 12/1986 | Kryter |
| 5,390,254 A * | 2/1995 | Adelman ............. 381/315 |
| 7,197,152 B2 | 3/2007 | Miller et al. |
| 7,204,800 B2 | 4/2007 | Easter et al. |
| 7,214,179 B2 | 5/2007 | Miller, III et al. |
| 7,354,394 B2 | 4/2008 | Slattery, III et al. |
| 7,489,793 B2 | 2/2009 | Miller, III et al. |
| 7,522,738 B2 | 4/2009 | Miller, III |
| 7,556,597 B2 | 7/2009 | Miller, III et al. |
| 8,641,595 B2 | 2/2014 | Basinger |
| 2001/0007050 A1 | 7/2001 | Adelman |
| 2002/0067838 A1 | 6/2002 | Kindred et al. |
| 2004/0172242 A1 | 9/2004 | Seligman et al. |
| 2005/0222487 A1* | 10/2005 | Miller et al. ........... 600/25 |

(Continued)

OTHER PUBLICATIONS

"Identify." Merriam-Webster.com. Merriam-Webster, n.d. Web. Sep. 24, 2015. <http://www.merriam-webster.com/dictionary/identify>.*

(Continued)

*Primary Examiner* — Charles A Marmor, II
*Assistant Examiner* — Carrie R Dorna
(74) *Attorney, Agent, or Firm* — Hauptman Ham, LLP

(57) ABSTRACT

A method for use in an implantable hearing instrument, including receiving an output signal from an implanted microphone implanted in a person, identifying a first characteristic of said output signal, based on said first characteristic, amplifying said microphone output signal by at least one of a plurality of gain settings to produce an amplified signal, wherein said plurality of gain setting comprise at least two different gain settings, inputting said amplified signal into a signal processor, processing said amplified signal to generate a transducer drive signal; and using said transducer drive signal to drive implanted auditory stimulation device implanted in a person to stimulate an auditory component.

23 Claims, 8 Drawing Sheets

(56) References Cited

U.S. PATENT DOCUMENTS

| | | |
|---|---|---|
| 2006/0155346 A1 | 7/2006 | Miller, III |
| 2006/0183965 A1 | 8/2006 | Kasic, II et al. |
| 2007/0021647 A1 | 1/2007 | Slattery, III et al. |
| 2007/0120722 A1 | 5/2007 | Nygard et al. |
| 2007/0282392 A1 | 12/2007 | Callias et al. |

OTHER PUBLICATIONS

Author Unknown, "Effective AGC Amplifier Can Be Built at a Nominal Cost", Electronic Design, Aug. 3, 1998.

James Staley, "60 dB Wide Dynamic Range, Low Frequency AGC Circuit Using a Single VGA", Analog Devices, 2007.

* cited by examiner

AUTOMATIC GAIN CONTROL FOR IMPLANTED MICROPHONE

CROSS REFERENCE

The present application is a continuation of and claims priority to U.S. patent application Ser. No. 12/357,183, filed Jan. 21, 2009, naming David Basinger as an inventor, which claims priority to U.S. Provisional Patent Application No. 61/022,390, filed on Jan. 21, 2008, also naming David Basinger as an inventor, the present application claiming priority to each of these applications, and the disclosures of each of these applications are hereby incorporated by reference herein by reference in their entirety.

BACKGROUND

In the class of hearing aid systems generally referred to as implantable hearing instruments, some or all of various hearing augmentation componentry is positioned subcutaneously on, within, or proximate to a patient's skull, typically at locations proximate the mastoid process. In this regard, implantable hearing instruments may be generally divided into two sub-classes, namely semi-implantable and fully implantable. In a semi-implantable hearing instrument, one or more components such as a microphone, signal processor, and transmitter may be externally located to receive, process, and inductively transmit an audio signal to implanted components such as a transducer. In a fully implantable hearing instrument, typically all of the components, e.g., the microphone, signal processor, and transducer, are located subcutaneously. In either arrangement, an implantable transducer is utilized to stimulate a component of the patient's auditory system (e.g., auditory ossicles and/or the cochlea).

By way of example, one type of implantable transducer includes an electromechanical transducer having a magnetic coil that drives a vibratory actuator. The actuator is positioned to interface with and stimulate the ossicular chain of the patient via physical engagement. (See e.g., U.S. Pat. No. 5,702,342). In this regard, one or more bones of the ossicular chain are made to mechanically vibrate, which causes the ossicular chain to stimulate the cochlea through its natural input, the so-called oval window.

As may be appreciated, a hearing instrument that proposes to utilize an implanted microphone will require that the microphone be positioned at a location that facilitates the receipt of acoustic signals. For such purposes, an implantable microphone may be positioned (e.g., in a surgical procedure) between a patient's skull and skin, for example, at a location rearward and upward of a patient's ear (e.g., in the mastoid region).

For a wearer a hearing instrument including an implanted microphone (e.g., middle ear transducer or cochlear implant stimulation systems), the skin and tissue covering the microphone diaphragm may increase the vibration sensitivity of the instrument to the point where body sounds (e.g., chewing) and the wearer's own voice, conveyed via bone conduction, may saturate internal amplifier stages and thus lead to distortion. Also, in systems employing a middle ear stimulation transducer, the system may produce feedback by picking up and amplifying vibration caused by the stimulation transducer.

Certain proposed methods intended to mitigate vibration sensitivity may potentially also have an undesired effect on sensitivity to airborne sound as conducted through the skin. It is therefore desirable to have a means of reducing system response to vibration (e.g., caused by biological sources and/or feedback), without affecting sound sensitivity. It is also desired not to introduce excessive noise during the process of reducing the system response to vibration. These are the goals of the present invention.

SUMMARY

For a wearer of an implantable hearing instrument (e.g., middle ear or cochlear stimulation systems) that incorporates an implantable microphone, undesirable vibration (e.g., non-ambient vibration) carried by the wearer's tissue (e.g., skull and/or soft tissue) may be detected and amplified by the implantable microphone to an undesirable degree. For instance, operation of a middle ear transducer used with a hearing instrument may create vibration that is transmitted by the skull to the microphone. In this case, detection and amplification of the vibration can lead to objectionable feedback. Unwanted vibration (e.g., in the skull or other tissue) can also arise naturally from talking or chewing. In both cases, undesired vibrations may be transmitted to the site of the implanted microphone where a component of these undesired vibrations may be received by a microphone diaphragm and amplified.

It is therefore one objective to reduce the response of such hearing instruments to unnaturally high vibrations (e.g., due to a patient's own voice), without necessarily or substantially affecting the response of the microphone to desired signals. Another objective is to map the entire output of a microphone having a relatively larger dynamic range into a signal processor having a relatively smaller dynamic range. Yet another objective is to improve the signal-to-noise ratio of an output signal of a microphone, to enhance the sound quality that a patient receives.

These and additional objectives are achieved by systems and methods (i.e., utilities) presented herein where an implantable hearing instrument system is operative to selectively alter/lower the gain of signals that have a magnitude above a predetermined threshold. In other words, unnaturally large vibrations (e.g., due to a patient's own voice) are amplified less than desired signals, so that a patient may experience a more representative sound.

According to one aspect of the present invention, an implantable hearing instrument system is provided that includes an AGC circuit. The AGC circuit may be any circuit that adjusts the gain of a signal from a microphone dependent on a characteristic of that signal. For example, the AGC may amplify a signal by a first value when the signal is below a predetermined threshold, and amplify the signal by a second value that is less than the first value when the signal is above the threshold. Additionally, the AGC may apply a non-linear function to the signal, such that larger signals are amplified relatively less than smaller signals.

According to a further aspect of the present invention, an implantable hearing instrument system is provided that includes an AGC circuit that amplifies a signal dependent upon the frequency content of the signal. For example, the AGC may be configured to reduce the amplification for signals that are above a predetermined threshold and in a predetermined frequency range (e.g., the frequency range of a patient's own voice). In this regard, larger signals that are due to a patient's own voice may be suppressed, while other large signals (e.g., outside the predetermined frequency range) may be unaffected.

According to a still further aspect of the present invention, an implantable hearing instrument system is provided that includes an AGC circuit that is configured to map the dynamic range of a microphone into the dynamic range of a signal processor. In one embodiment, this is achieved by reducing the gain that is applied by the AGC to relatively large signals (e.g., signals above a predetermined threshold) so that the output signal of the microphone is "compressed." Additionally, the AGC may be configured to communicate information about the gain applied to the signals to a signal processor, so that the signal processor may account for the gain applied when conditioning the signals to be output to a transducer.

According to another aspect of the invention, an implantable hearing instrument is provided that is operative to identify own voice events and dynamically adjust the gain of a microphone input signal provided to a signal processor of the device. In one arrangement an output of an accelerometer is monitored to determine an own voice event. If a signal characteristic exceeds a predetermined value, an own voice event is identified and gain applied to a microphone output signal may be reduced. In one particular arrangement, an accelerometer output signal is compared to the microphone output signal to determine the own voice event. In another arrangement, only a predetermined frequency range of the accelerometer output signal is monitored to determine the own voice event. In a yet further arrangement, a non-linear gain is applied across the frequency range of the microphone output signal.

According to another aspect of the present invention, an implantable hearing instrument system is provided that includes an AGC circuit coupled to a microphone, wherein the microphone is physically separated from the AGC. In this embodiment, the output signal of the microphone is amplified at a location near the microphone. In this regard, the signal-to-noise ratio may be improved when electromagnetic interferences are present in the coupling between the microphone and the AGC circuit. Additionally, the signal may also be attenuated prior to being fed into the AGC circuit.

DETAILED DESCRIPTION

Reference will now be made to the accompanying drawings, which at least assist in illustrating the various pertinent features of the present invention. In this regard, the following description of a hearing aid device is presented for purposes of illustration and description. Furthermore, the description is not intended to limit the invention to the form disclosed herein. Consequently, variations and modifications commensurate with the following teachings, and skill and knowledge of the relevant art, are within the scope of the present invention. The embodiments described herein are further intended to explain the best modes known of practicing the invention and to enable others skilled in the art to utilize the invention in such, or other embodiments and with various modifications required by the particular application(s) or use(s) of the present invention.

Figure 1:
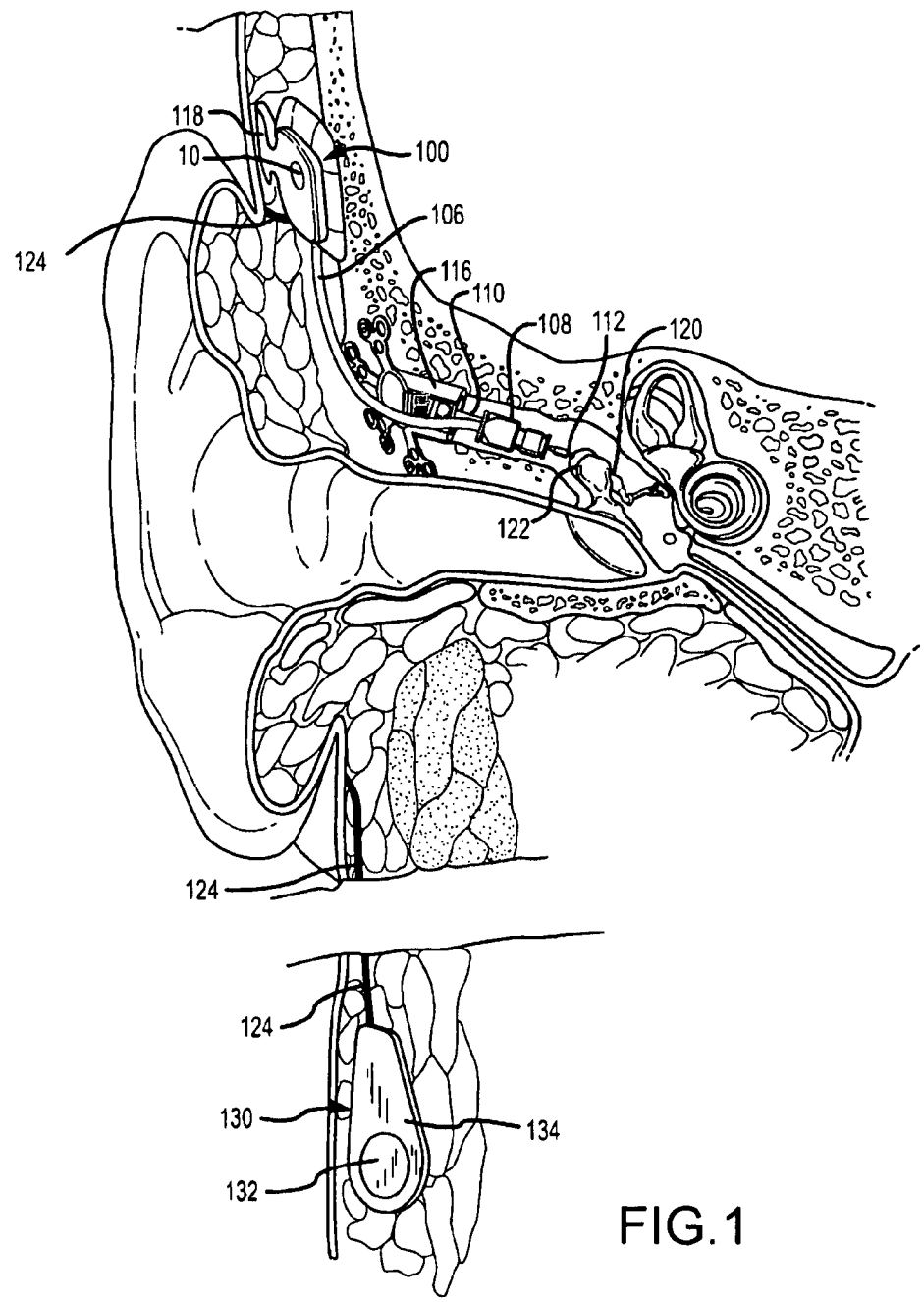
FIG. 1 illustrates a fully implantable hearing instrument.
Figure 2:
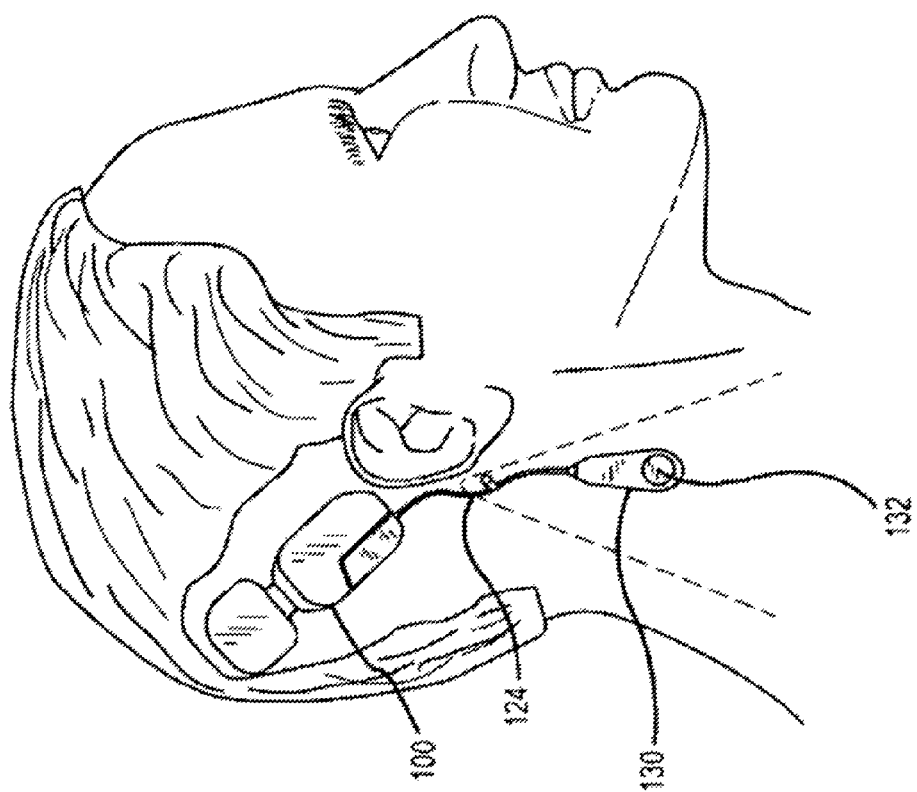
FIG. 2 illustrates one embodiment of a soft tissue mount of a microphone.

FIGS. 1 and 2 illustrate one application of the present invention. As illustrated, the application comprises a fully implantable hearing instrument system. As will be appreciated, certain aspects of the present invention may be employed in conjunction with semi-implantable hearing instruments as well as other fully implantable hearing instruments (e.g., cochlear implant systems), and therefore the illustrated application is for purposes of illustration and not limitation.

In the system illustrated in FIGS. 1 and 2, a biocompatible implant housing 100 is located subcutaneously on a patient's skull. The implant housing 100 includes a signal receiver 118 (e.g., comprising a coil element) and is interconnected to a microphone assembly 130 via a signal wire 124, which is typically a multi-conductor cable. The implant housing 100 may be utilized to house a number of components of the implantable hearing instrument. For instance, the implant housing 100 may house an energy storage device and a signal processor. Various additional processing logic and/or circuitry components may also be included in the implant housing 100 as a matter of design choice. In the present arrangement, the signal processor within the implant housing 100 is electrically interconnected via a signal wire 106 to a transducer 108.

The transducer 108 is supportably connected to a positioning system 110, which in turn, is connected to a bone anchor 116 mounted within the patient's mastoid process (e.g., via a hole drilled through the skull). The transducer 108 includes a connection apparatus 112 for connecting the transducer 108 to an auditory component of the patient. In the present embodiment, the transducer is connected to the ossicular chain 120. However, it will be appreciated that connection to another auditory component (e.g., oval window, round window, cochlea, etc.) is possible and within the scope of the present invention. In a connected state, the connection apparatus 112 provides a communication path for acoustic stimulation of a portion of the ear, such as the ossicles 120, e.g., through transmission of vibrations to the incus 122 or other ossicles bone.

The microphone assembly 130 may be spaced from the implant housing 100 such that it need not be mounted to the skull of a patient. Such spacing may facilitate vibration attenuation. Stated otherwise, mounting the microphone assembly 130 relative to soft tissue of the patient may isolate the microphone assembly 130 from one or more sources of non-ambient vibrations (e.g., skull-borne vibrations). The microphone assembly 130 includes a diaphragm 132 that is positioned to receive ambient acoustic signals through overlying tissue, a microphone transducer (not shown) for generating an output signal indicative of the received ambient acoustic signals, and a housing 134 for supporting the diaphragm 132 relative to the transducer. As shown, the wire 124 interconnecting the implant housing 100 and the microphone assembly 130 is routed subcutaneously behind the ear of the patient. However, it will be appreciated that in other embodiments other microphone assemblies may be utilized including, without limitation, skull mounted microphones and/or microphones that are integrated into the implant housing 100.

During normal operation, acoustic signals are received subcutaneously at the diaphragm 132 of the microphone assembly 130. The microphone converts sound pressure levels into proportional electric signals. Microphones are generally specified according to the transfer function involved which is commonly on the order of −55 dBV/0.1 pa. The microphone will usually also include some electrical noise floor and is often specified at its equivalent input noise (EIN). For example, the microphone may have an EIN of 25 dBSPL. Converting sound pressures to a proportional electrical value requires the following equation:

dBVout=dBSPLin−(74 dB−(−55 dBV/0.1 pa))

where 0.1 pa is equivalent to 74 dBSPL. For example, 25 dBSPL converts to 25 dBSPL−(74 dBSPL+(55 dBV/0.1 pa)) =−104 dBV. This is also the electrical equivalent of the stated EIN level in dBV. Therefore, a 25 dBSPL EN converts to −109 dBV. This provides the lower limit of the microphone's performance. The upper limit of the microphone is at least 115 dBSPL or −19 dBV. This implies a dynamic range 206 of −109 dBV−(−19 dBV)=90 dB for the microphone. See FIG. 3.

The microphone assembly 130 generates an output signal that is indicative of the received acoustic signals. The output signal is provided to the implant housing 100 via the signal wire 124. Upon receipt of the output signal, a signal processor within the implant housing 100 processes the signals to provide a processed audio drive signal via a signal wire 106 to the transducer 108. As will be appreciated, the signal processor may utilize digital processing techniques to provide frequency shaping, amplification, compression, and other signal conditioning, including conditioning based on patient-specific fitting parameters. The audio drive signal causes the transducer 108 to transmit vibrations at acoustic frequencies to the connection apparatus 112 to effect the desired sound sensation via mechanical stimulation of the incus 122 of the patient.

If the dynamic range 205 of the DSP is 80 dB, some portion 210 of the microphone signal must be lost or removed or clipped before the dynamic range of the microphone will "fit" into the DSP. Clipping the microphone signals that are above the maximum input requirement for the DSP will cause distortion and other unwanted sounds to the patient.

The microphone diaphragm is exposed directly to overlying patient tissue, which creates a mass loading effect. This mass loading creates a high sensitivity to mechanical vibrations and other externally induced mechanical movements that deflect the diaphragm and result in large microphone output signals (i.e., electrical signals). Such vibrations may be caused by the user's own voice, operation of the implanted transducer, and/or the positional movement of the user. For instance, walking induces a low frequency pulse on the microphone diaphragm and normal daily movements such as showering, hair brushing or simply rubbing/scratching can result in very large output signals.

Normal vibrations that are induced in the skull due to the users' vocalizations can be mitigated, at least in part, by measuring non-acoustic vibrations with a transducer (e.g., accelerometer, second microphone diaphragm, etc.) and subtracting the transducer signal from the microphone output signal. The signal remaining after applying this cancellation technique is proportional to the acoustic sounds that generated the microphone output signal. Use of such a cancellation technique is adequate under most normal circumstances. However, in some non-normal circumstances microphone saturation and/or clipping can occur. Such non-normal circumstances include unusually loud vocalizations or external stimulus (e.g., a gunshot). In most applications, the microphone and its amplifier, if any, has a large dynamic range and is amplified for normal operation in such a way that the highest expected signal (e.g., normal acoustic levels) arriving from the microphone at the signal processor of the hearing instrument will be near the highest amplitude that signal processor can accept without saturating. This optimizes the available dynamic range of the hearing instrument.

Unusually large vibrations or other non-normal circumstances produce microphone output signals that are higher than the signal processor can accept. This saturates the input of the signal processor in such a way that no normal acoustic information can be analyzed. One solution to prevent this situation has been to lower the gain of the microphone amplifier such that the output signal cannot saturate the signal processor. However, a reduction of the gain of the microphone output signal may make it difficult for a user to perceive low amplitude acoustic sounds.

In addition to problems associated with saturation of the signal processor, some patients may experience an unusually loud sound due to vibrations caused by their own voice. For example, some patients may experience a sound that is in the range of 90-110 dB, which is approaching the level of a gunshot. Clearly, this is an undesirable operation for the wearer of an implantable hearing instrument. Again, one remedy is to attenuate the signal from the microphone for all acoustic signals. However, this has drawbacks in speech recognition and/or general sound perception.

A hearing aid of any kind has a primary function: to enable the patient to hear and understand speech. This allows the user to participate in everyday human interactions normally. Speech is generally in the range of 55-75 dBSPL. It is also useful to hear low level sounds. That is, shuffling papers, the click of a knob, and other such low level sounds are useful auditory feedback and assist in everyday situations. Such low level sounds are generally in the range of 20-30 dBSPL. Collectively, these sound levels may be termed useful sound levels.

Loud sounds (e.g., gun shots, hammering, etc.) are generally above 100 dBSPL. Such sounds, while helpful to alert a hearing aid user of environmental conditions, need not be 120 dBSPL in order to perform the warning function. To summarize, it is desirable to enhance sounds from about 20 dBSPL to about 95 dBSPL. Sounds above 95 dBSPL have limited utility to the patient and therefore can be selectively reduced as can the unusually loud own voice response some patients encounter. These sound ranges are approximate and it will be appreciated that this range could in either direction for particular applications and requirements.

Presented herein is a system and method for dynamically altering the gain of a microphone output signal to allow for enhancing the gain applied to useful sounds while reducing the gain applied to loud sounds. Generally, a feedback circuit nonlinearly alters the gain of a microphone output signal. The system allows for sharp attenuation of gain during non-normal circumstances without attenuating gain during normal circumstances. The perceived sound produced by this arrangement is similar to how the inner ear reacts to large amplitude sounds. In a normal hearing person, the tensor tympani muscle adds tension to the ossicular chain to muffle vibrations that are being transmitted to the stapes footplate. This is similar in that the effect is essentially an attenuation in the gain of a normal ear. The system also allows for mapping the dynamic range of the microphone into the dynamic range of the signal processor to reduce or eliminate clipping.

Figure 4:
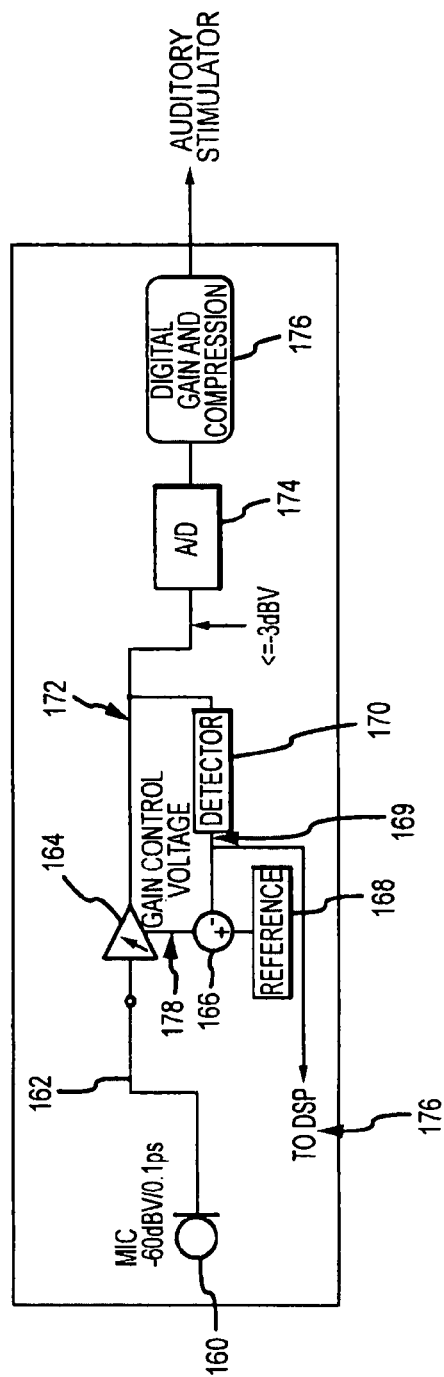
FIG. 4 illustrates a block diagram of one embodiment of a fully implantable hearing instrument.

In one embodiment, the gain of the hearing system is dynamically varied by an automatic gain control (AGC) circuit, which automatically adjusts the gain of an amplifier based on a characteristic of an input signal. FIG. 4 is a block diagram that illustrates an exemplary implantable microphone and hearing instrument system that includes an AGC circuit. In operation, a signal is input to a controllable gain amplifier 164 from an implantable microphone 160 through a conductor 162. The amplifier 164 is operable to amplify the signal received from the implantable microphone 160 by a factor that is dependent upon a control signal the amplifier receives from a gain control voltage node 178. To form the control signal, the output of the amplifier 164 is first fed to a detector circuit 170. The detector circuit 170 is operable to sense the magnitude (e.g., a root-mean-square (RMS) value, an absolute value, etc.) of the output signal from the amplifier 164. The detector circuit 170 may then output the sensed value to a subtractor 166 where the signal is subtracted from a reference voltage 168. The output of the subtractor 166 is then fed into the amplifier 164 through the gain control voltage node 178. In this regard, the gain of the amplifier 164 may be controlled by comparing the output signal on the node 172 with the reference voltage 168. The output signal from the amplifier 164 is also fed through an analog-to-digital (A/D) converter 174, a signal processor 176, and then to an auditory stimulator, such as the transducer 108 shown in FIG. 1. As indicated by reference numeral 169, the signal to the DSP 176 branches off from the output of the subtractor 166 prior to reaching the detector 170 in an exemplary embodiment.

Figure 3:
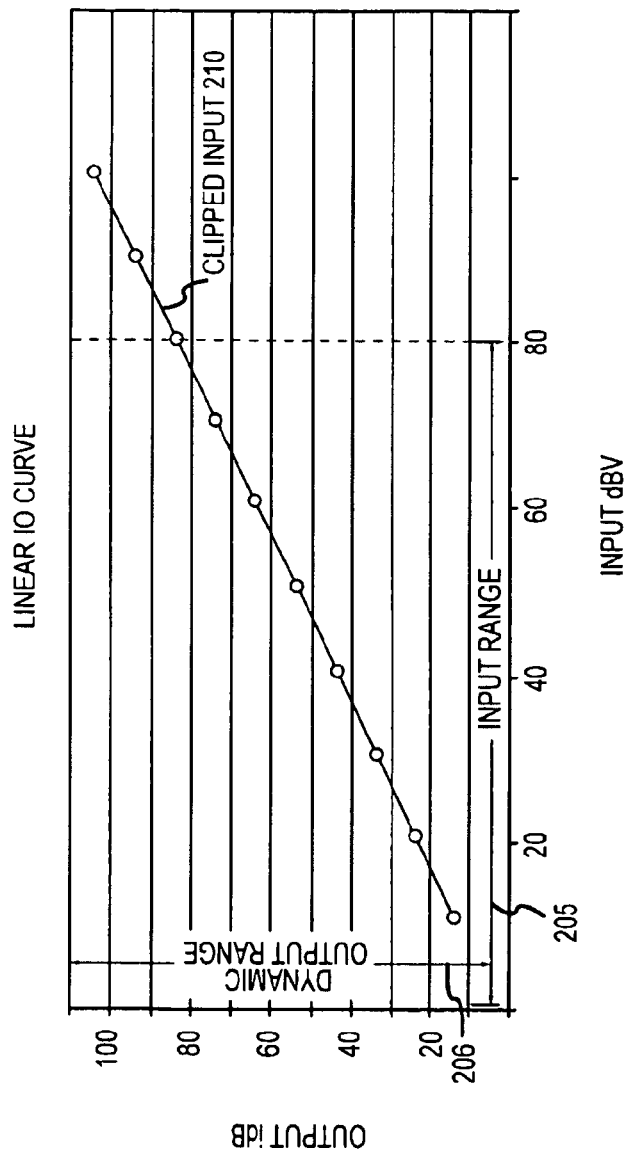
FIG. 3 illustrates a linear input output curve of one combination of a microphone and DSP.
Figure 5:
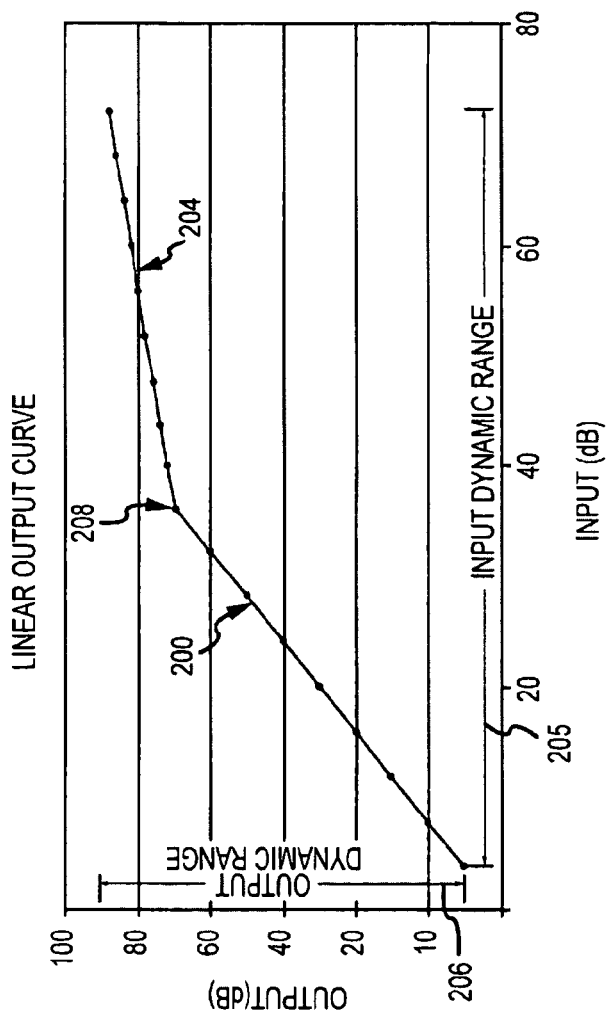
FIG. 5 illustrates a non-linear gain input output curve of one embodiment of a fully implantable hearing instrument.

FIG. 5 illustrates a transfer function for an exemplary implantable hearing instrument system that includes an AGC circuit, such as the system shown in FIG. 3. The horizontal axis represents the input signal of the amplifier 164 (i.e., the node 162 of FIG. 3), while the vertical axis represents the output signal of the amplifier 164 (i.e., the node 172 of FIG. 3). As can be seen, the gain of the amplifier is a first value (e.g., slope) when the input is below a certain reference level (i.e. the threshold point 208), which is indicated by the portion of the line 200. In one arrangement, the threshold point 208 is programmably adjustable. When the input is greater than the threshold point 208, the gain of the amplifier 164 is reduced to a second value (e.g., slope) that is less than the first value, indicated by the portion of the line 204 that has a slope that is less than the portion of the line 200. As can be appreciated, this configuration permits very large signals (e.g., unnaturally loud signals due to a patient's own voice) to be amplified at a lower amplification level than smaller signals. Furthermore, lowering the amplification for larger signals may permit the full dynamic range 205 of the microphone 160 to "fit" into the dynamic range 206 of the signal processor 176, which has the effect of reducing distortion, and ultimately producing a higher quality sound for the patient. For instance, the 110 dB dynamic range of the exemplary microphone may be compressed into the 80 dB dynamic range of the signal processor. Although the transfer function shown in FIG. 5 is a piecewise linear function, those having skill in the art will readily recognize that other functions may be implemented in accordance with the present invention. As an example, a nonlinear transfer function may be used.

As shown in FIG. 3, the output of the detector 170 may also be fed to the signal processor 176. This may be desirable so that the signal processor 176 may compensate for the gain that was applied to the signal. In this regard, the signal processor 176 may be able to produce a more representative sound by using the information provided by the output of the detector 170.

The detector 170 may also be operable to sense not only the magnitude of the output of the amplifier, but also the frequency content. For example, the detector 170 may be configured to sense signals that are in the frequency range of a patient's voice (e.g., 0-4 kHz). To achieve this, one or more filters may be used (e.g., a low pass filter positioned between the node 172 and the detector 170 shown in FIG. 3). In one arrangement, a notch filler may be utilized that is set to the upper and lower frequency ranges of a user's voice. In this regard, the AGC may be used primarily to lower the amplification of a patient's own voice, while not affecting the amplification of other larger signals.

In another embodiment, the signal processor 176 may be used to implement the filtering function. For example, in response to an unnaturally loud sound at a relatively narrow frequency (e.g., due to a patient's own voice), the AGC 164 may attenuate, or reduce the amplification of all frequency bands to prevent saturation. When the attenuated signal is then fed to the signal processor 176, the signal processor 176 may sense the frequency content of the unnaturally loud sound, and correspondingly increase the amplification of other signals outside of that frequency band. In this manner, only signals due to the patient's own voice, or other undesirable signals, are suppressed. As can be appreciated, the AGC function in this embodiment is shared by the AGC hardware 164 and the signal processor 176.

Figure 6:
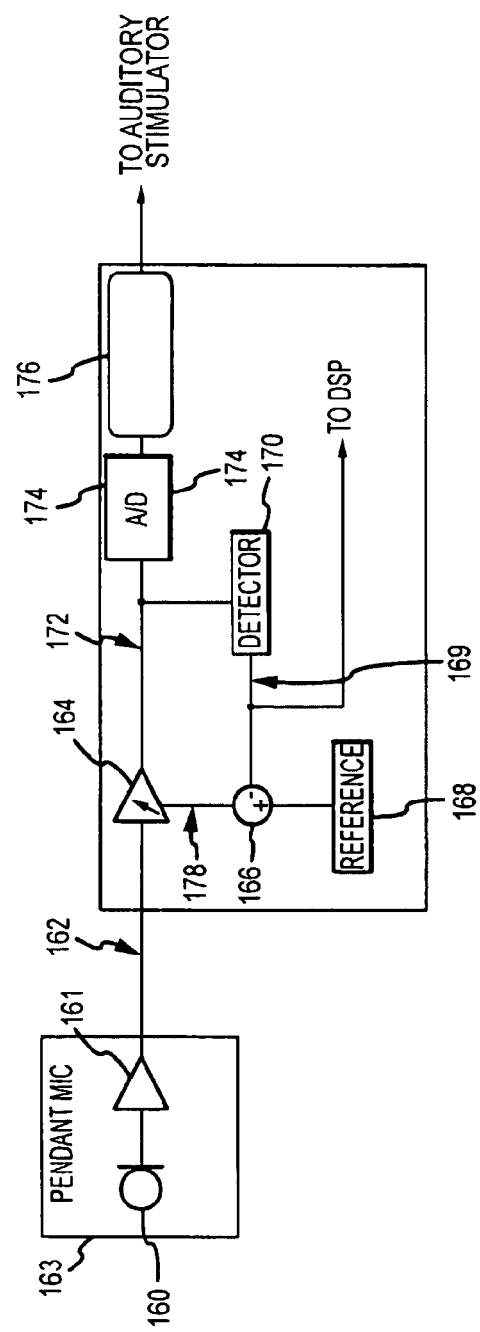
FIG. 6 illustrates a block diagram of another embodiment of a fully implantable hearing instrument.

FIG. 6 illustrates another block diagram of an exemplary implantable hearing instrument system that includes an AGC circuit. Various components that are common to those discussed in reference to FIG. 3 are numbered alike. Accordingly, only differences in the present system are discussed herein. In this embodiment, the pedant microphone 160 is coupled to the amplifier 164 through a cable 162. The cable 162 may pick up unwanted electromagnetic interference (EMI) signals. The useful signals originating from the microphone can be very small, on the order of, for example, <1 m volt. Such small signals can, in some instances, be drown out by EMI interface. To reduce the effect of these unwanted signals, an amplifier 161 in the pedant enclosure 163 may first amplify the signal from the microphone 160. By amplifying the signal prior to it leaving the pendant enclosure 163, the difference between the microphone output signals and the EMI noise signals is increased. Furthermore, the output signal may also be attenuated prior to being fed to the processor or AGC to prevent saturation. This serves the function of increasing the signal-to-noise ratio (SNR) of the signal that enters the amplifier 164, which improves the sound quality of the system.

Figure 7:
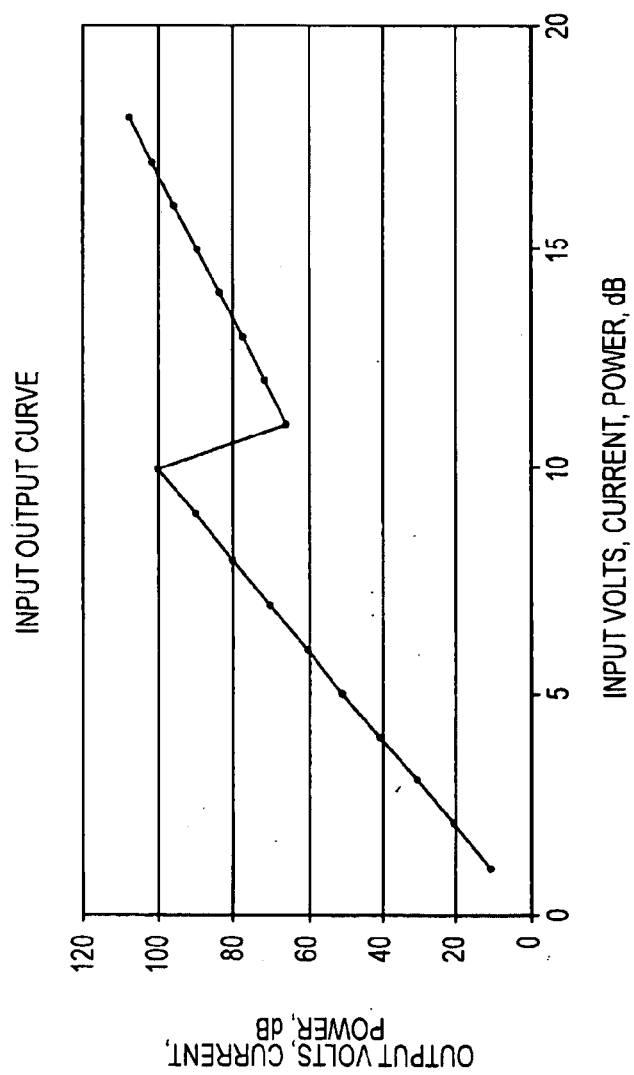
FIG. 7 illustrates a non-linear gain input output curve of another embodiment of a fully implantable hearing instrument.

In an alternate arrangement, a non-linear gain functionality may me implemented in another in a standard voltage divider network. That is, a pseudo AGC function can be realized by a variable attenuator instead of utilizing an amplifier. In this method, all signals are optionally amplified first. The resulting signal is then fed to a voltage divider network in which one of the resistors/impedances is varied depending on the signal amplitude or power. A resistor divide network attenuates relatively low signal levels by a small amount and large signal levels by a large amount or vice versa. The input output curve for such a system is illustrated in FIG. 7

As noted above, it is sometimes desirable to cancel noise signals form the microphone output signal. Generally a vibration response of an accelerometer is matched to the vibration response of the microphone to achieve cancellation. The cancellation compares the signal of the microphone and accelerometer and attempts to cancel any common signals. An example of such a system is set forth in U.S. patent Ser. No. 11/565,001 entitled "Dual Feedback Control System For Implantable Hearing Instrument" the entire contents of which are incorporated herein by reference. Own voice however, will be a common signal and under some conditions (e.g., patient dependent) will be greater than the airborne sound. The airborne sound will contain essentially the same content, own voice, as the vibration signal. The algorithm may not be able to distinguish between the airborne and tissue borne. It may be necessary to sense the presence of own voice and reduce the signal level input into the DSP. The patient would then hear his own voice at a reduced volume and consequently all other sounds will be reduced. Alternatively, the system may reduce the volume/amplification only in the frequency range of the voice of the user. In such an arrangement, the volume of sounds outside this frequency range are not reduced.

Figure 8:
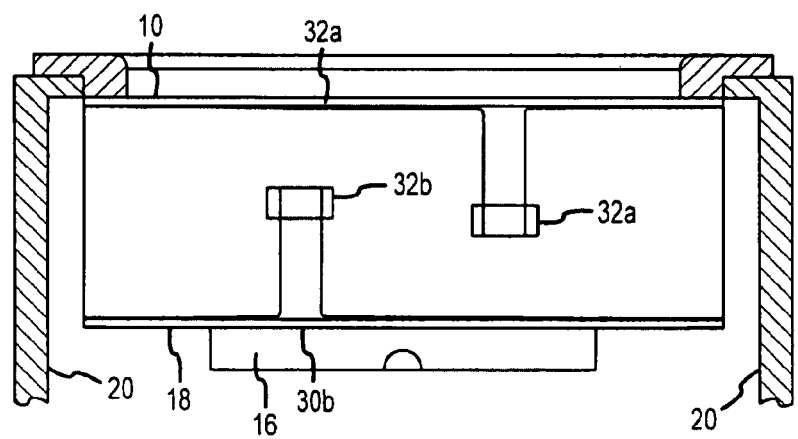
FIG. 8 illustrates a microphone and accelerometer for use in identifying own voice events.

FIG. 8 illustrates a microphone assembly that is operative to provide a signal indicative of acceleration/vibration that may subsequently be removed from a combined response from a microphone diaphragm, which includes an acceleration response and an ambient sound response. As shown, the microphone assembly utilizes a first diaphragm 10 that is positioned to be responsive to acoustic signals and acceleration/vibration received through overlying tissue and generate a first output indicative of the acoustic and acceleration signals. More specifically, the microphone diaphragm 10 deflects relative to a first enclosed space. This deflection results in a pressure fluctuation that is monitored by a first microphone element 32A. Accordingly, the microphone element 32A generates a first electrical output corresponding to the movement of the microphone diaphragm 10.

The microphone assembly also includes a cancellation diaphragm 18 that is mass loaded with a cancellation mass 16 (e.g., proof mass). The cancellation diaphragm is a vibration sensitive element (e.g., accelerometer) that is disposed inside of the microphone housing 20 such that it is substantially isolated from ambient acoustic signals. The mass loading allows the cancellation diaphragm 18 to deflect in response to acceleration forces applied to the housing 20. Specifically, the cancellation diaphragm deflects relative to a second enclosed space 30B in response to acceleration. This deflection results in a pressure fluctuation in the second enclosed space 30B that is monitored by a second microphone element 32B. Accordingly, the second microphone element 32B generates a second electrical output corresponding to the movement of the cancellation diaphragm 18.

Generally, the first microphone diaphragm is directed toward the "wanted" sound. For example, the first diaphragm may be disposed towards overlying tissue to receive ambient acoustic sounds. The second microphone diaphragm is directed toward an unwanted sound source. For example, the second microphone diaphragm may be directed inward to detect the users own voice or other non-ambient vibrations. Both microphone diaphragms may detect both sources of sound but each receives the majority of its signal from the source it is directed toward. This enables the unwanted sound to be subtracted from the wanted or ambient signal. If, however, the unwanted sound becomes sufficiently loud as to dominate both microphones, then the cancellation will no longer faithfully reproduce the speech. Instead it will simply amplify the unwanted sound. Such an arrangement is possible if the users own voice dominates both microphones. In this situation, the AGC circuitry can be utilized such that if the microphones sense essentially the same level of signal and these signals are sufficiently loud then the amplification will be compressed (switched to a lesser amplification mode) under these conditions.

In an alternate arrangement, the output signal of the second microphone diaphragm (or other accelerometer) may be monitored to identify when large amplitude non-ambient signals are present. If the non-ambient signals exceed a predetermined threshold, it may be assumed the user is speaking and the amplification of the input signal may be reduced based on the presumed own voice event. Further, such monitoring (which may be done within the DSP) may be frequency based such that only identified signals within a predetermined frequency range result in a change (e.g., reduction) in amplification.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A method for use in an implantable hearing instrument, comprising:
   receiving a microphone output signal from an implanted microphone implanted in a person;
   receiving an accelerometer output signal from an accelerometer;
   identifying a first characteristic of interest in at least one of said accelerometer output signal or said microphone output signal, and, upon the identification, adjusting a gain setting;
   amplifying said microphone output signal using said gain setting to produce an amplified signal;
   processing said amplified signal to generate a drive signal; and
   using said drive signal to drive an implanted auditory stimulation device implanted in the person to stimulate an auditory component, wherein
   the action of identifying the first characteristic of interest entails identifying a characteristic indicative of an own voice event as differentiated from a characteristic indicative of other types of body noise.

2. The method of claim 1, wherein:
   the action of identifying the first characteristic of interest entails identifying a presence of bone conducted own voice noise.

3. The method of claim 1, wherein the action of amplifying the microphone signal comprises:
   amplifying a first frequency portion of said microphone output signal associated with a voice of the person using a first gain setting and amplifying at least a second frequency portion of said microphone output signal with a second gain setting, where said second gain setting is larger than said first gain setting.

4. The method of claim 1, wherein the identified first characteristic is an amplitude of the accelerometer output signal resulting from the person speaking.

5. The method of claim 1, wherein the identified first characteristic is a characteristic of the accelerometer output signal resulting from the person speaking as distinguished from a characteristic of the accelerometer output signal resulting from the person not speaking.

6. The method of claim 1, wherein the action of adjusting the gain setting is based on the identified first characteristic of interest.

7. The method of claim 6, further comprising subsequently determining that the characteristic of interest is not present in a subsequently received accelerometer output signal or a subsequently received microphone output signal, and subsequently readjusting the gain based on the subsequent determination.

8. The method of claim 1, wherein the action of amplifying the microphone output signal is executed using an amplifier, and wherein the action of adjusting the gain setting entails adjusting a gain of the amplifier.

9. The method of claim 1, wherein the action of identifying a first characteristic of interest in at least one of said accelerometer output signal or said microphone output signal corresponds to comparing said accelerometer output signal to said microphone output signal, the method further comprising:
subsequent to the action of identifying, cancelling at least a portion of said microphone output signal based on said accelerometer output signal.

10. The method of claim 1, further comprising:
in addition to the action of identifying, cancelling at least a portion of said microphone output signal based on said accelerometer output signal.

11. The method of claim 1, wherein the action of identifying the first characteristic of interest entails at least one of qualitatively or quantitatively identifying a first characteristic of interest.

12. A method for use in an implantable hearing instrument, comprising:
receiving a microphone output signal from an implanted microphone implanted in a person;
receiving an accelerometer output signal from an accelerometer;
identifying a first characteristic of interest in at least one of said accelerometer output signal or said microphone output signal, and based upon the identification, adjusting a gain setting from a previous setting;
amplifying said microphone output signal using said gain setting to produce an amplified signal;
processing said amplified signal to generate a drive signal; and
using said drive signal to drive an implanted auditory stimulation device implanted in the person to stimulate an auditory component, wherein at least one of:
the action of amplifying said microphone output signal using said gain setting entails amplifying first frequencies of the microphone output signal less than second frequencies of the microphone output signal, wherein the second frequencies are different than the first frequencies;
the action of amplifying said microphone output signal using said gain setting entails amplifying frequencies corresponding to the frequencies of the person's own voice received by the microphone differently than other frequencies; or
the action of adjusting the gain setting entails reducing a gain setting of the hearing instrument relative to that which was the case prior to the identification of the first characteristic of interest;
wherein at least one of the respective output signals is a signal resulting from the person speaking in a first instance, the method further includes:
receiving a second microphone output signal from the implanted microphone implanted in a person;
receiving a second accelerometer output signal from the accelerometer;
wherein at least one of the respective second output signals results from the person speaking in a second instance, and
the first characteristic is distinguished from a second characteristic of the respective second output signals, the second characteristic being different from the first characteristic.

13. A method for use in an implantable hearing instrument, comprising:

receiving a microphone output signal from an implanted microphone implanted in a person;
receiving an accelerometer output signal from an accelerometer;
identifying a first characteristic of interest in at least one of said accelerometer output signal or said microphone output signal, and, upon the identification, adjusting a gain setting;
amplifying said microphone output signal using said gain setting to produce an amplified signal;
processing said amplified signal to generate a drive signal; and
using said drive signal to drive an implanted auditory stimulation device implanted in the person to stimulate an auditory component;
wherein: the first characteristic of interest corresponding to at least one of an amplitude or frequency as compared to other amplitudes or frequencies that are not of interest; and
the action of adjusting the gain setting entails adjusting the gain setting from that used by the instrument with respect to those other amplitudes or frequencies.

14. The method of claim 13, wherein identifying a first characteristic comprises: monitoring a predetermined frequency band of said output signal of said accelerometer.

15. The method of claim 14, wherein said predetermined frequency band comprises a frequency band associated with a voice of the person of the hearing instrument.

16. The method of claim 13, wherein:
the action of identifying the first characteristic of interest entails identifying the occurrence of an own-voice event.

17. The method of claim 13, wherein:
the actions of identifying a first characteristic of interest in at least one of said accelerometer output signal or said microphone output signal, and, upon the identification, adjusting the gain setting entails determining that the first characteristic of interest is present in at least one of said accelerometer output signal or said microphone output signal, and, upon the determination, adjusting the gain setting.

18. The method of claim 17, wherein:
the action of determining that the first characteristic of interest is present in at least one of said accelerometer output signal or said microphone output signal entails determining that the first characteristic of interest is present in at least one of said accelerometer output signal or said microphone output signal that distinguishes the respective signal from other possible respective signals; and
the action of adjusting the gain setting entails adjusting the gain setting to a first gain setting as differentiated from another gain setting previously used by the implantable hearing instrument in the absence of the determination.

19. The method of claim 17, wherein:
the action of determining that the first characteristic of interest is present in at least one of said accelerometer output signal or said microphone output signal entails determining that the first characteristic of interest is present in at least one of said accelerometer output signal or said microphone output signal that distinguishes the respective signal from other possible respective signals.

20. The method of claim 17, wherein:
the action of adjusting the gain setting entails adjusting the gain setting to a first gain setting as differentiated from another gain setting previously used by the implantable hearing instrument in the absence of the determination.

21. The method of claim 13, wherein:
wherein the first characteristic is a non-normal characteristic, and the action of setting the gain entails setting the gain to a non-normal gain setting as differentiated from a gain setting that would be used in the absence of the identification of the first characteristic of interest.

22. The method of claim 13, wherein:
the action of identifying the first characteristic of interest entails at least one of qualitatively or quantitatively determining that the respective signals include features indicative of the occurrence of an own-voice event based on an analysis of the respective output signals.

23. The method of claim 13, further comprising analyzing at least one of the output signals to identify that the first characteristic of interest in at least one of said accelerometer output signal or said microphone output signal is present, wherein
the action of analyzing occurs before the action of processing.

* * * * *